Figure 1:
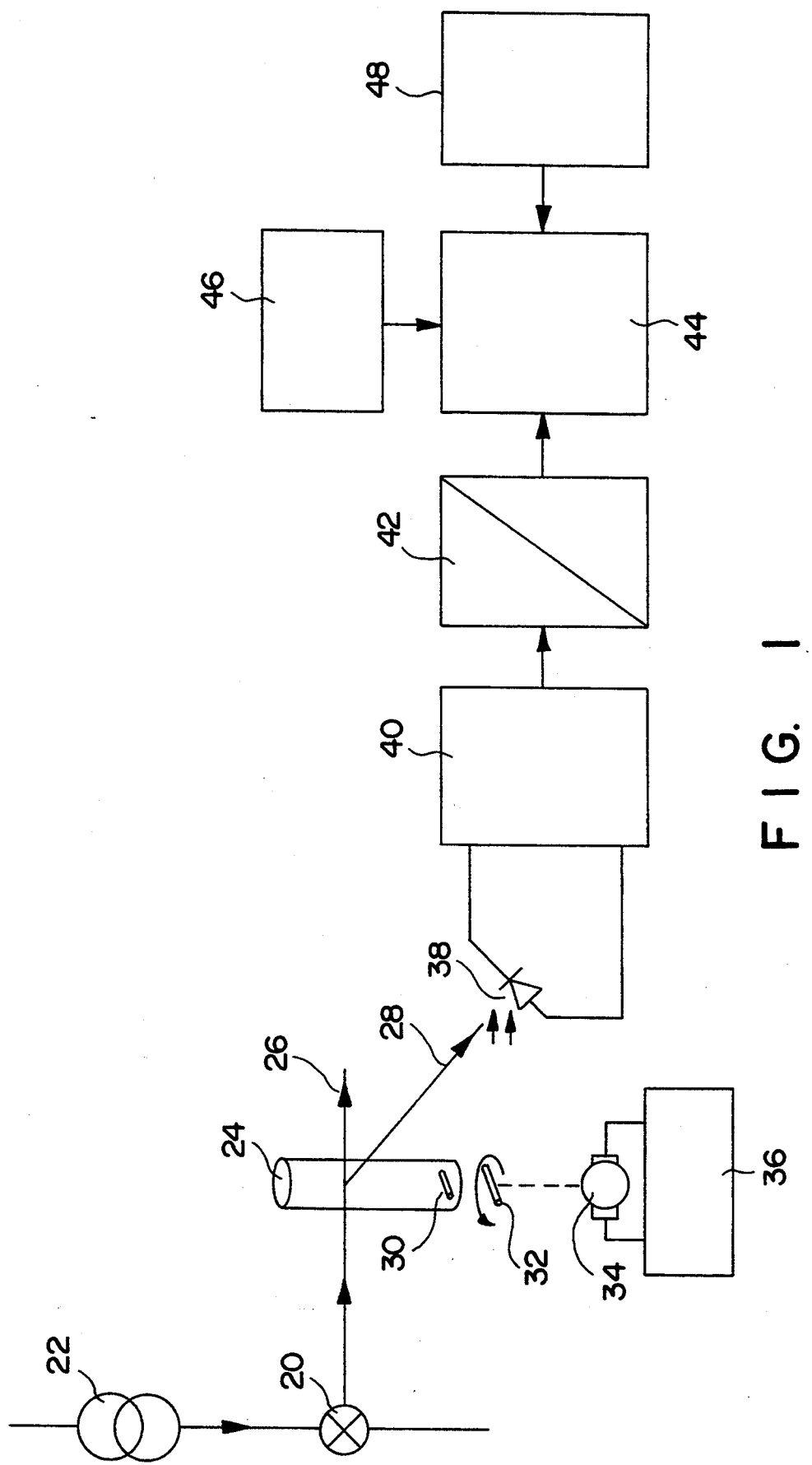

United States Patent [19]

Plagge et al.

[11] Patent Number: 5,412,470
[45] Date of Patent: May 2, 1995

[54] DISPERSION PHOTOMETER, IN PARTICULAR FOR THE KINETIC DETERMINATION OF TOTAL PROTEINS

[75] Inventors: Heinrich Plagge, Dransfeld; Hans-Joachim Krause, Göttingen; Dietmar Oberdorfer, Göttingen; Ulrich Plüquett, Göttingen, all of Germany

[73] Assignee: Dosatec GmbH, Germany

[21] Appl. No.: 952,712

[22] PCT Filed: May 27, 1991

[86] PCT No.: PCT/DE91/00451
 § 371 Date: Dec. 21, 1992
 § 102(e) Date: Dec. 21, 1992

[87] PCT Pub. No.: WO91/19184
 PCT Pub. Date: Dec. 12, 1991

[30] Foreign Application Priority Data
May 30, 1990 [DE] Germany .......... 40 17 465.4

[51] Int. Cl.⁶ .......................... G01N 21/51
[52] U.S. Cl. .................. 356/338; 356/341
[58] Field of Search .......... 356/338, 339, 341

[56] References Cited

U.S. PATENT DOCUMENTS

| | | | |
|---|---|---|---|
| 2,436,262 | 2/1948 | Miller | 356/339 |
| 4,136,953 | 1/1979 | Klein et al. | 356/339 |
| 4,157,871 | 6/1979 | Anderson et al. | 356/341 |
| 4,250,394 | 2/1981 | O'Connor | 356/340 |
| 4,408,880 | 10/1983 | Tsuji et al. | 356/338 |

FOREIGN PATENT DOCUMENTS
4932 11/1965 Australia .

Primary Examiner—Richard A. Rosenberger
Attorney, Agent, or Firm—Eckert Seamans Cherin & Mellott

[57] ABSTRACT

The dispersion photometer described is designed particularly for the kinetic determination of total proteins and has a light source (20), an optical system, a removable optical cell (24) in the sample chamber, a stirrer, a photo-electric sensor (38) which receives light scattered forward at an angle, and an electronic processing and display unit (46) connected in series with the photo-electric sensor (38). All the elements located between the light source (20) and the optical cell (24), and between the optical cell (24) and the photo-electric sensor (38), have a coefficient of transmission or reflection in the visible region of the spectrum which is as high as possible, and do not reflect or absorb selectively.

11 Claims, 3 Drawing Sheets

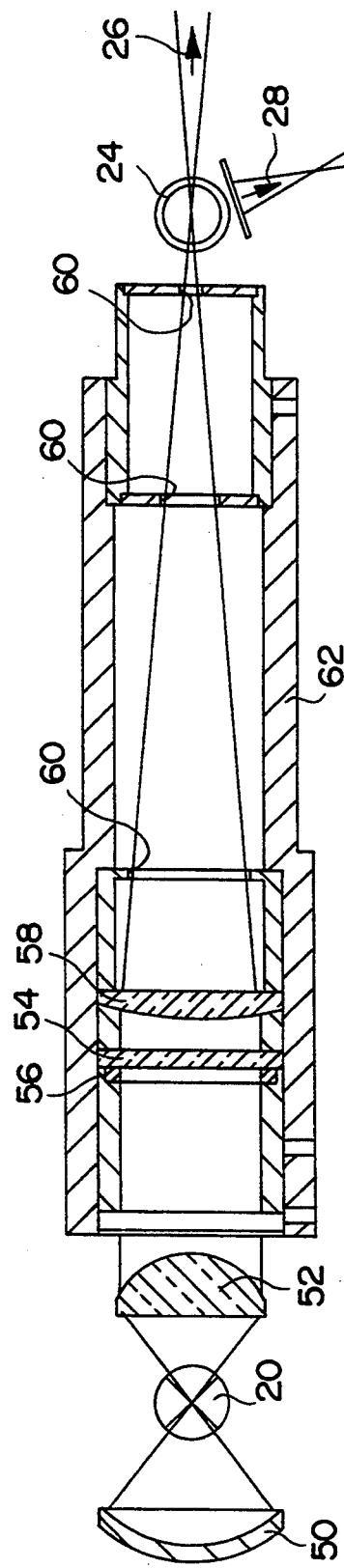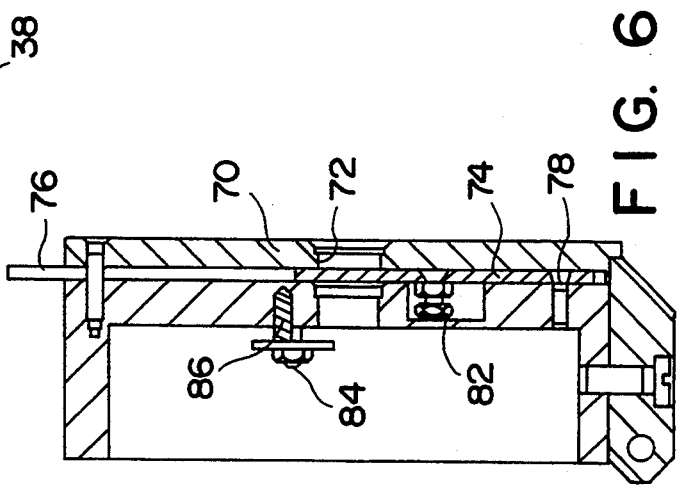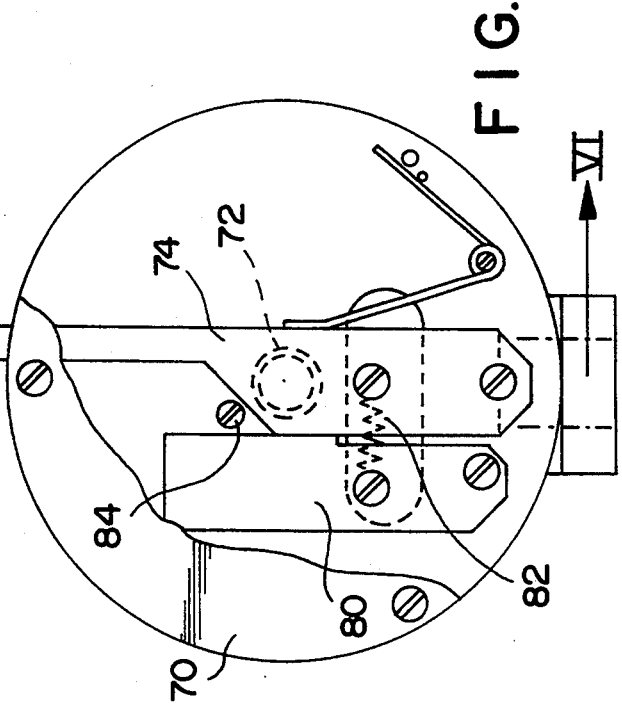

DISPERSION PHOTOMETER, IN PARTICULAR FOR THE KINETIC DETERMINATION OF TOTAL PROTEINS

The invention refers to a dispersion photometer (nephelometer), in particular for the kinetic determination of total proteins, having (a) a light source, (b) an optical system which projects the image of the light source into the sample chamber, (c) a removable optical cell in the sample chamber, into which the liquid to be analyzed can be given, (d) a stirrer, which stirs the liquid to be analyzed during the measurement, (e) a photo-electric sensor which receives light scattered in an forward angle, and (f) an electronic processing and display unit following this photo electric sensor for measuring the values of the dispersed light.

Dispersion photometers of this type are principally known, as an example it is referred to an article of F. Wittmann and G. Traxler "Neue Perspektiven der nephelometrischen Proteinbestimmung (Vorstellung ARRAY)" in Labormedizin 9 (1986) 434–436 ("New perspectives of the nephelometric protein determination" (presentation ARRRAY)). In the market available dispersion photometers are very expensive, their price is currently clearly above DM 100.000, - - . This fact has proven to be an obstacle for the use of dispersion photometers in laboratories for medical analysis, although the analysis with a dispersion photometer is more sensitive, faster, more precise and generally also lower in cost than an analysis following the conventional methods in clinical chemistry.

Reiber has described in Fresenius Z Anal Chem. (1982) 311: 374–375 a new physical-chemical principle for the determination of protein concentrations in biological samples, in which the precipitation of protein is carried out in trichloroacetic acid (TCA), and instead of measuring the absorption (turbidity) the dispersed light is measured. The precipitation of protein molecules causes initially an increase of dispersing particles with a dimension which is small compared to the wavelength 1 of the used light. Therefore the dispersed light intensity I increases, for which is valid $I \simeq 1/1^4$. In the course of the precipitation more and more larger particles show up, the dimension of the particles is now not any more small compared to the wavelength of the measuring light, whereby a different dispersion is prevalent, for which is valid $I \approx 1/1^2$.

Due to the dependance of the intensity of the dispersed light from the wavelength so far only more or less monochrome light was applied and in addition only light in the short wavelength range of the visual spectrum has been employed. In order to achieve the required sensitivity, which means a low measurement limit of 20 mg/l or less, which is expected by the users, it is required to apply high standards of technology for optics and electronics. This also explains the high price level for known dispersion photometers.

Starting from these considerations the invention is based upon the task, to further develop and modify a dispersion photometer of the above described type in such a way, that the optical system and the electronic unit is simplified.

This task is solved starting from a dispersion photometer of the type described above by inserting between light source and optical cell and between optical cell and photo-electric sensor only such (optical) elements, which allow a maximum transmission respectively reflection without selective absorption or reflection in the visual spectral range (400 nm to 800 nm).

Based upon this invention the sample in the optical cell is illuminated with white light. This has the advantage, that the light flux of the illuminating light is substantially higher than with so far known instruments. Due to the high light flux of the illuminating light also the intensity of the dispersed light is high, allowing to use low cost, long term stable photo-electric sensors as detectors. Therefore complicated measures for the optic system and for the electronic processing unit are not required.

As a surprise came the fact, that it is possible to leave the up to now as required considered principle of mainly monochrome light and the use of light of short wavelength, without leaving the principle of measurement. This fact could not be expected in view of the principally existing dependance of the intensity of the dispersed light from the wavelength on one hand, and in view of the specific differences of the wavelength dependance of the two occurring types of dispersion on the other hand. By using white light the measurement includes wavelengths, in which, e.g., for the red light, the light source has a radiation intensity which is clearly higher than at the short wavelength range. Therefore by using white light the intensity of the illumination is increased and in addition the range of high quantum yield of the photo-electric sensor is used.

By using white light the optical system can be kept very short, and therefore the system becomes rather simple. For example it is sufficient to use a 10 Watts Halogen lamp as light source, to which a collimator, in case of need a concave mirror behind the lamp, and a collecting lens as optical components are attached. The length of the total optical system is thereby less than 20 cm, if a lens of a focal length of approx. 10 cm is used.

The photo-electric sensor is arranged as close as possible at the optical cell, in order to detect dispersed light in an angle as wide as possible. As photo-electric sensors made of silicon are relatively small, the detector can be put also because of reasons of available space close to the optical cell, and requires little space. Therefore the size of the total optical system is determined mainly by the illuminating unit and the sample chamber, and their distance from each other. Therefore the invented dispersion photometer can be made relatively small in size, the complete instrument has a size of 34×30×14 cm.

In a preferred embodiment a collimating lens, a heat protective filter, and a projection lens in a tube, which has at lease one fixed aperture and is colored in non reflective black, are installed between light source and optical cell. This arrangement ensures, that light can only reach the optical cell: light beams which pass beside the optical cell and might lead to an undesired signal in the photo-electric sensor, will then be absorbed. The optical system has few elements and is simple, and therefore reduces the danger of undesired reflections.

In a further improvement it is proposed to transfer the output signal of the photo-electric sensor to an A/D converter, where for a displayed measured value n sequentially and in short time intervals collected individual measurements are taken, stored, and arranged by magnitude in such a way, that only n/2, preferably n/3 measurements with the smallest values are taken into account and displayed after averaging as measured value. In the practical situation of the dispersion measurement the light dispersed by the protein coagulating in TCA is superposed by short term dispersed light signals, caused by pollutions in the sample, pollutions of the TCA and of eventual dilutions of TCA. These dispersed light signals add to the momentarily performed measurement. As the solution in the optical cell is being rotated, these signals cause only short term dispersed light signals. By not taking into account at least half of the electric signals received, this means at least all higher signal values, it is achieved that such erroneous dispersed (scattered) light signals practically cannot influence the total result, i.e. the measured value.

As photo-electric detector preferably a silicon-photoelement is being used. Its output signal can be transferred without intermediate storage directly to an A/D converter, as the signal of the photo-electric detector does not change during the time of conversion of a measurement signal. In a further advantageous step a current/voltage converter is arranged between the silicon photo-electric detector and the A/D converter.

It has proven to be very advantageous to provide a dispersion photometer, which has a normally closed opening for a pipette above the optical cell, by which pipette the substance to be tested can be injected into the optical cell, with a lock system which locks the opening, if there is no optical cell in the sample chamber, and allows to open the opening if there is an optical cell in the sample chamber. By this measure it is avoided, that a liquid can be pipetted into the sample chamber if there is no optical cell in it. Pipetting into the sample chamber would require a very extensive cleaning process and in addition cause hygienic dangers.

It is also advantageous to arrange all optical elements on a rigid base plate. This leads on one hand to a precise attachment of all optical elements, on the other hand the optical unit can be premounted and tested prior to insertion into the instrument housing, and service and repair can be carried out at all optical elements by taking out the complete optical unit from the instrument housing.

Finally it is also advantageous to put all optical elements in a separate chamber of the instrument housing. Therefore on one hand the electrical components are separated from the optical components, on the other hand an effective cooling is possible. As based on this invention a 10 Watts Halogen lamp is used, the generated heat is anyhow lower than at known instruments which mostly work with more powerful lamps. In an advantageous further step of the invention there are openings close to the lamp for the cooling, and accordingly openings at the opposite end of the optical system. In front of the opening is a fan, which maintains a continuous air flow longitudinal to the optical unit, which results in an effective and practically fully sufficient cooling.

Figure 3:
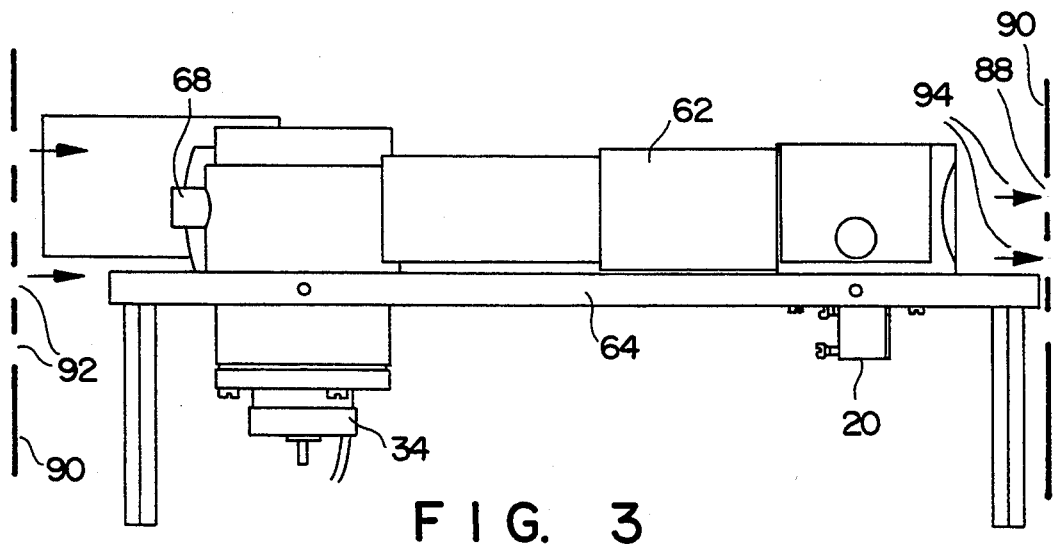
Figure 4:
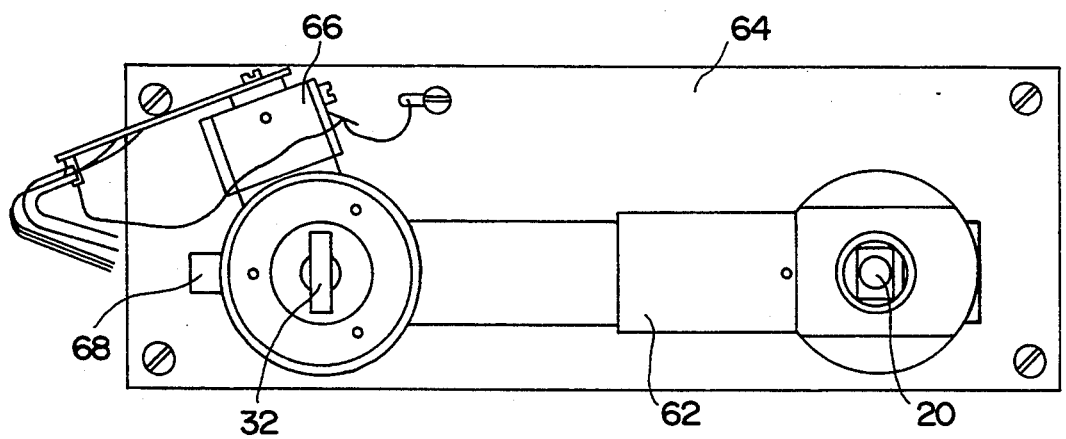
Figure 7:
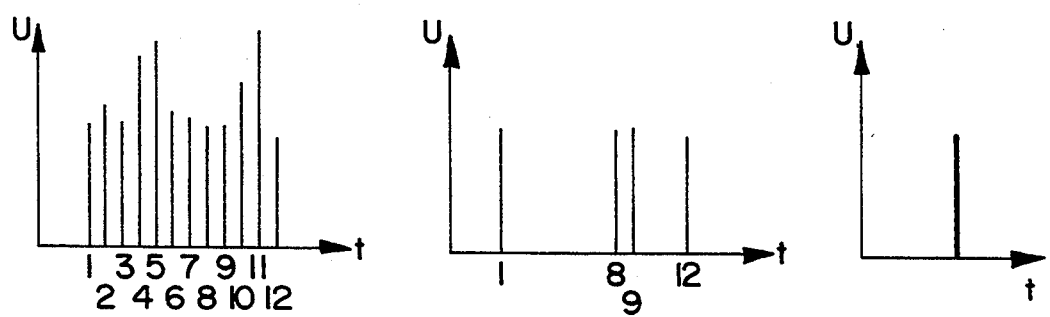

Further advantages and features of the invention are apparent from the other claims and the following description of a non-limiting example, which is explained in detail with reference to the drawing. The drawing shows in:

FIG. 1 a circuit diagram of the dispersion photometer,

FIG. 2 a cross-section through the optical system,

FIG. 3 a side view of the complete optical system,

FIG. 4 a top view of the optical system according to FIG. 3,

FIG. 5 a top view on the holder of the optical cell, partially as cross-section, FIG. 6 a cross-section of the optical cell holder along intersection line VI—VI of FIG. 5 and FIG. 7 a diagrammatic presentation of 12 measurement values and their processing.

FIG. 1 shows the basic arrangement of the components of the dispersion photometer according to the invention. A light source 20 in the form of a 6 Volt/10 Watt Halogen lamp is powered by a constant current source 22 with constant current. The emitted light is focussed by a still to be described optics into the center of an optical cell, the optical cell has a diameter of approx. 7 mm, and is cylindric. The incident light passes through the optical cell, as shown by an arrow 26. Proteins in the optical cell, but also pollutions and similar, cause a dispersed light, which is shown as an arrow 28. It is detected in a 70° forward angle. In the optical cell there is also a stirrer 30 made of permanent magnetic or ferromagnetic material, to which a magnetic stick 32 is related, which is rotated by a stirrer motor 34, powered by a voltage source 36.

The dispersed light (arrow 28) impinges on a photoelectric sensor 38 in the form of a silicon photo element BPX 79. Its electric contacts are attached to a current-/voltage converter 40, whose output is coupled to an A/D converter 42. The individual measurement values which are now in digital form are then processed in a processor unit 44, which is described later in detail. Based on a multitude of individual measurement values one measured value is displayed on a display 46, where it is shown in the form of dispersed light units or in the form of a protein concentration. The processing unit 44 can be controlled by a keyboard 48.

In the following the optical unit is described. FIG. 2 shows the halogen lamp 20, to which an IR-permeable concave mirror 50 is attached in a distance of the double of the focal length. It is manufactured by superficially depositing evaporized metal and reflects in the visual spectral range (400 to 800 nm) almost free of energy losses and non-selective, and therefore independent from the wavelength. To the right the light is focussed (parallelized) by an aspheric glass lens 52 (collimator lens). The lens 52, too, has a high transparency in the visual spectral range, and shows no selective absorption or reflection therein, and allows therefore also to let pass the visual light independent from the wavelength.

A heat absorption filter 54 follows, it is of type KG 1 and manufactured by the company of Spindler and Hoyer, it is almost without color, and therefore has a practically wavelength-independent transmission in the visual spectral range. A noticeable absorption starts only for wavelengths above 1 p.m. The heat absorption filter 54 is, as shown in FIG. 2, mechanically fixed by using a rubber ring 56 in such a way that thermal expansion is possible.

In a short distance follows a flat convex lens 58 made of glass, it has a focal length of approx. 10 cm. A material. BK 7 of the a.m. company Spindler and Hoyer is used for this lens, the transmission in the visual spectral range is practically constant.

In the distance of the focal length and behind the flat convex lens 58 is the center of the optical cell 24. The light cone between parts 58 and 24 is limited by three circular apertures 60, of which one is as close as possible at the optical cell 24, another close to the flat convex lens 58, and a third one between these two apertures.

As can be seen from FIG. 2, the parts 54 to 60 ar mounted in a light-tight tube. As FIGS. 3 and 4 show, also the complete optical system is to a large extent sealed and therefore light-tight. FIGS. 3 and 4 show, that the complete optical system is mounted on a rigid base plate 64, which is fixed to the ground plate of the instrument housing (indicated in FIG. 3) by bolts and can be mounted respectively dismounted with few manipulations. FIGS. 3 and 4 show the sample chamber, in which the optical cell is arranged during the measurement. It is open towards the top. The photo-electric sensor 38 is mounted in an adapter 66 in a light-tight way close to the sample chamber, there are two apertures in the adapter 66, too, (see FIG. 2) between the sample chamber and the detector. The sample chamber is underneath closed by a stirring motor 34, when looking into the sample chamber the stirrer 32 can be recognized. Furthermore a tube 68 is mounted to the sample chamber, in which transmitted light (following the sense of the arrow 26 in FIG. 1) is absorbed without reflection. For the light source a prefocussed socket is used, which allows to exchange the light source without realignment.

The top of the sample chamber is closed by a pipette holder in a light-tight way, see FIGS. 5 and 6. Underneath is a cuvette holder which accepts the optical cell, it is not visible from the figures.

The pipette holder is closed on the top by the circular plate 70, which has a central opening 72, also called passage. This opening is normally closed by a lever 74, which has a handle 76 which can be rotated clockwise starting from the position shown around an axis 78. A second lever 80 is arranged on the left side of lever 74, and is rotatable around an axis, too. Both levers 74, 80 are connected elastically by a spring 82. Underneath the circular plate 70 a lock is provided, which consists mainly of a screw 84 and of springs 86. The springs push a disk connected to a screw downwards, thus the head of the screw 84 remains below the area of movement of the levers 74, 80. If in this situation the lever 74 is rotated by using the handle 76, the second lever 80 follows automatically with the consequence, that the entrance to the opening 72 remains locked.

However, if there is an optical cell in the sample chamber, the screw 84 is pushed upwards, its head is inserted in the area of movement of the second lever 80. If in this condition the lever 74 is rotated, the second lever 80 cannot follow this movement, the entrance of the opening 72 is free, a pipette, by which the liquid to be tested can be injected, can be inserted therethrough.

A multitude of other mechanical or electro-mechanical solutions are possible, in order to lock the entrance to the opening 72, if there is no optical cell in the sample chamber. For example the second lever 80 can be avoided, if the screw 84 is mounted at the other side of the lever 74 and if the lever 74 has a slit for the screw head and the screw shaft, which is made such, that the screw is above the surface of the circular plate 70 in the case of a missing optical cell and therefore stops the clockwise movement of the lever 74, however, as soon as the screw 84 is pushed further more upwards, its head is in front of a canal, which is suitable for the screw and its head, thus allowing a movement of the lever 74. In a further alternative a micro switch in the sample chamber recognizes the presence of the optical cell. This micro switch effects a relay which controls the entrance to the opening 72.

FIG. 7 shows the evaluation of obtained individual measurement data to one measured value. In the shown example it is assumed that twelve individual measurements collected in short intervals have been digitized by the A/D converter. The cycle time of the converter used in the practical example is 160 ms. The total of twelve signals (left side of diagram of FIG. 7) are evaluated in respect to their magnitude. Only ⅓ of the twelve signals, namely a group of 4 signals (middle side of the diagram of FIG. 7) are then processed, they are selected by the property that they represent the four lowest-value measurement data. Described in a different way only the four lowest data are being processed, the eight data with higher values are not taken into account. After averaging these the four selected individual data one measured value is obtained, which is shown in the right side of the diagram of FIG. 7.

This measured value is then displayed or stored and compared to other measured values obtained in a similar way.

Finally in FIG. 3 there are exit slits 88 in an instrument housing 90 close to the light source 20 and entrance slits 92 at the other end of the optical system. For simplification reasons a fan is not shown. Arrows 94 indicate an air flow.

We claim:

1. A dispersion photometer (nephelometer) for kinetic determination of total proteins in a liquid, comprising: (a) a light source, (b) an optical system including means for projecting and focusing the image of the light source into a sample chamber, (c) a removable optical cell in the sample chamber, into which the liquid can be given, (d) a photo-electric sensor for receiving light scattered in a forward angle, and (e) an electronic processing and display unit following the photo-electric sensor for processing and displaying the scattered light values including an A/D converter coupled to the photo-electric sensor for providing a digitized signal in response to an output signal from the photo-electric sensor and processing means for storing and evaluating n digitized signals according to their magnitude and for averaging no more than half of the n digitized signals having the smallest magnitudes for obtaining a displayed measured value, the dispersion photometer characterized in that between the light source and the optical cell and between the optical cell and the photo-electric sensor there are only such components, which in a spectral range (400 to 800 nm) exhibit a maximum transmission and a reflection without selective absorption or reflection, and in that a stirrer is provided for stirring the liquid during the determination.

2. The dispersion photometer according to claim 1, wherein a collimator lens, a heat absorption filter and an imaging lens are arranged between the light source and the optical cell.

3. The dispersion photometer according to claim 1, having above the optical cell a normally locked opening for a pipette, by which pipette a substance to be tested can be injected in the optical cell, further comprising a locking system which locks the opening if there is no optical cell in the sample chamber and which allows the opening to open if there is an optical cell in the sample chamber.

4. The dispersion photometer according to claim 1, wherein all optical components are attached to a rigid base plate.

5. The dispersion photometer according to claim 1, wherein the optical components are in a separate chamber of the instrument housing, there are exit openings for air close to the light source, there is a fan close to the lamp, and entrance openings for air are provided.

6. The dispersion photometer according to claim 1, wherein the photo-electric sensor is connected to an A/D converter.

7. The dispersion photometer of claim 6, characterized in that a current/voltage converter is arranged between the photo-electric sensor and the A/D converter.

8. The dispersion photometer of claim 1, characterized in that the processing means averages about one third of the n digitized signals having the smallest magnitudes.

9. A dispersion photometer for measuring total proteins in a liquid, comprising:
- a light source;
- a sample chamber, including a removable optical cell in the sample chamber for holding the liquid;
- an optical system, including means for projecting and focusing an image of the light source into the sample chamber;
- a stirrer for stirring the liquid;
- a photo-electric sensor responsive to light scattered in a forward angle from the optical cell;
- an A/D converter for providing a digitized signal in response to an output signal from the photo-electric sensor;
- a processor for storing n digitized signals, evaluating the n digitized signals according to their magnitudes, and averaging no more than about n/2 of the n digitized signals having the smallest magnitudes to provide a displayed measured value; and,
- display means for displaying the displayed measured value, the dispersion photometer being characterized in that between the light source and the optical cell and between the optical cell and the photo-electric sensor there are only such optical elements that exhibit a maximum transmission and a reflection without selective absorption or reflection in a wavelength range between about 400 nm and about 800 nm.

10. The dispersion photometer of claim 9, characterized in that the output signal is coupled to the A/D converter by a current/voltage converter.

11. The dispersion photometer of claim 9, wherein the sample chamber is characterized by a normally locked opening above the optical cell for a pipette, by which pipette a substance to be tested can be injected into the optical cell, the opening being characterized in that a locking system for locking the opening if there is no optical cell in the sample chamber and for allowing the opening to open if there is an optical cell in the sample chamber.

* * * * *